US012569049B2

(12) United States Patent
Chevalier

(10) Patent No.: US 12,569,049 B2
(45) Date of Patent: Mar. 10, 2026

(54) DEFORMABLE ABSORBENT SUBSTRATE FOR A PACKAGING AND/OR APPLICATION ASSEMBLY FOR A COSMETIC PRODUCT

(71) Applicant: L V M H RECHERCHE, Saint Jean de Braye (FR)

(72) Inventor: Marc Chevalier, Franconville (FR)

(73) Assignee: L V M H RECHERCHE, Saint Jean de Braye (FR)

( * ) Notice: Subject to any disclaimer, the term of this patent is extended or adjusted under 35 U.S.C. 154(b) by 825 days.

(21) Appl. No.: 17/254,716

(22) PCT Filed: Jun. 20, 2019

(86) PCT No.: PCT/FR2019/051512
§ 371 (c)(1),
(2) Date: Dec. 21, 2020

(87) PCT Pub. No.: WO2019/243748
PCT Pub. Date: Dec. 26, 2019

(65) Prior Publication Data
US 2021/0267347 A1 Sep. 2, 2021

(30) Foreign Application Priority Data

Jun. 21, 2018 (FR) ...................................... 18 55526

(51) Int. Cl.
*A45D 33/00* (2006.01)
*A45D 34/04* (2006.01)
(Continued)

(52) U.S. Cl.
CPC ........... *A45D 33/006* (2013.01); *A45D 34/04* (2013.01); *A45D 40/26* (2013.01); *A61K 8/0208* (2013.01);
(Continued)

(58) Field of Classification Search
CPC ...... A45D 40/26; A45D 34/04; A45D 33/006; A45D 33/025; A45D 2200/1036;
(Continued)

(56) References Cited

U.S. PATENT DOCUMENTS 3,570,036 A 3/1971 Gilchrist et al.
4,698,871 A 10/1987 Patkos
(Continued)

FOREIGN PATENT DOCUMENTS

CN 107048670 A 8/2017
EP 1314373 A2 5/2003
(Continued)

OTHER PUBLICATIONS

Translation of WO 2018/007758 (Year: 2018).*
(Continued)

*Primary Examiner* — Monica A Huson
(74) *Attorney, Agent, or Firm* — von Briesen & Roper, s.c.

(57) ABSTRACT
The invention relates to a deformable absorbent substrate for a packaging and/or application assembly for a cosmetic product, having cells defined by ridges. The ridges may be created in particular by means of additive manufacturing, in particular by selective laser sintering, selective laser fusion, stereolithography, or fused filament fabrication.

19 Claims, 8 Drawing Sheets

(51) Int. Cl.

| | | |
|---|---|---|
| *A45D 40/26* | (2006.01) |
| *A61K 8/02* | (2006.01) |
| *A61Q 19/00* | (2006.01) |
| *B33Y 80/00* | (2015.01) |
| *B65B 3/04* | (2006.01) |

(52) U.S. Cl.
CPC .............. *A61Q 19/00* (2013.01); *B33Y 80/00* (2014.12); *B65B 3/04* (2013.01); *A45D 2200/1036* (2013.01); *A61K 2800/10* (2013.01); *A61K 2800/87* (2013.01)

(58) Field of Classification Search
CPC .. A61Q 19/00; A61K 8/0208; A61K 2800/87; A61K 2800/01; B65B 3/04; B33Y 80/00
See application file for complete search history.

(56) References Cited

U.S. PATENT DOCUMENTS

| | | | | |
|---|---|---|---|---|
| 2007/0277844 | A1* | 12/2007 | Gueret | ................... A45D 33/02 |
| | | | | 132/320 |
| 2016/0183660 | A1* | 6/2016 | Kim | ....................... A45D 40/22 |
| | | | | 428/137 |
| 2018/0098919 | A1 | 4/2018 | Pallari et al. | |

FOREIGN PATENT DOCUMENTS

| | | | |
|---|---|---|---|
| EP | 1397974 | A1 | 3/2004 |
| EP | 2837374 | 81 | 12/2017 |
| FR | 2860960 | A1 | 4/2005 |
| FR | 3039378 | A1 | 2/2017 |
| JP | 2003144223 | A | 5/2003 |
| JP | 2010505503 | A | 2/2010 |
| JP | 3198102 | U | 6/2015 |
| JP | 2016536099 | A | 11/2016 |
| JP | 2017508086 | A | 3/2017 |
| WO | 9728718 | A1 | 8/1997 |
| WO | 0176410 | A1 | 10/2001 |
| WO | 2009018435 | A1 | 2/2009 |
| WO | 2017016608 | A1 | 2/2017 |
| WO | 2017017228 | A1 | 2/2017 |
| WO | 2017033797 | A1 | 3/2017 |
| WO | 2017078204 | A1 | 5/2017 |
| WO | 2018007758 | A1 | 1/2018 |

OTHER PUBLICATIONS

International Search Report related to Application No. PCT/FR2019/051512; reported on Sep. 10, 2019.
"EOS Materials Plastic", www/eos.info/material-p, Status Mar. 2016.

* cited by examiner

DEFORMABLE ABSORBENT SUBSTRATE FOR A PACKAGING AND/OR APPLICATION ASSEMBLY FOR A COSMETIC PRODUCT

CROSS-REFERENCE TO RELATED APPLICATION

This Application is a 35 USC § 371 US National Stage filing of International Application No. PCT/FR2019/051512 filed on Jun. 20, 2019 and claims priority under the Paris Convention to French Patent Application No. 18 55526 filed on Jun. 21, 2018.

FIELD OF THE DISCLOSURE

The present invention relates to a deformable absorbent substrate intended to be impregnated with a cosmetic product. The invention also concerns a packaging and/or application assembly for a cosmetic product, comprising such an absorbent substrate. The invention also relates to a method for producing such an absorbent substrate and such a packaging assembly for a cosmetic product.

PRIOR ART

For the purposes of the present invention, "cosmetic product" is understood to mean a cosmetic product intended to be applied to a human being. A "cosmetic product" is more generally a product as defined in Regulation (EC) No. 1223/2009 of the European Parliament and of the Council, dated Nov. 30, 2009, relating to cosmetic products.

Application FR 3,039,378 describes an example of a packaging assembly for a cosmetic product, comprising an absorbent substrate capable of being impregnated with cosmetic product. Such an absorbent substrate prevents in particular any unexpected flow of the cosmetic product, the product being released by contact of an applicator with the absorbent substrate and pressure on the absorbent substrate.

According to FR 3,039,378, the absorbent substrate is an open-cell sponge or of a material with woven or non-woven fibers. These materials have a good capacity for impregnation with cosmetic product. However, they generally allow redistributing or releasing only a portion of the cosmetic product with which they are impregnated. This results in a significant loss of cosmetic product, which cannot be used.

More generally, there is a need for an absorbent substrate for a packaging assembly for a cosmetic product, for which the characteristics—in particular the absorbency and degree of recovery—can be determined more precisely.

BACKGROUND OF THE DISCLOSURE

To this end, a deformable absorbent substrate is described for a packaging and/or application assembly for a cosmetic product, the absorbent substrate having cells defined by ridges, the ridges being created by additive manufacturing.

Thus, advantageously, the production of such an absorbent substrate, in particular by an additive manufacturing process, makes it possible to obtain much finer and better controlled characteristics than those of an absorbent substrate made of a sponge material or a woven or non-woven textile material.

According to preferred embodiments, the absorbent substrate comprises one or more of the following features, alone or in combination:

the ridges are created by selective laser sintering, selective laser melting, stereolithography, or fused filament fabrication;

with the substrate extending in a main direction, the ridges are shaped to extend substantially in a same plane when the absorbent substrate is compressed by pressure in the main direction;

the ridges are cylindrical with a polygonal cross-section, in particular square or hexagonal, round or oblong;

the ridges are interconnected by hinges, also created by additive manufacturing, preferably concurrently with the ridges, where appropriate;

with the substrate extending in a main direction, the absorbent substrate has a first layer in which the absorbent substrate has first cells and a second layer in which the absorbent substrate has second cells different from the first cells;

the first and second cells are:
  of different shapes; and/or
  of different volumes;

with the absorbent substrate extending in a main direction, the absorbent substrate has at least one layer, oriented perpendicularly to the main direction, said at least one layer having third cells and fourth cells, the fourth cells being different from the third cells;

the third and fourth cells are:
  of different shapes; and/or
  of different volumes;

the substrate comprises a skin on at least one of its surfaces, the skin preferably having fluidtight portions, the skin more preferably being fluidtight over its entire surface, the skin being integral with the rest of the absorbent substrate or being attached to the rest of the absorbent substrate;

the absorbent substrate being of substantially cylindrical shape, extending in a main direction of extension, a side skin is created on the side face of the absorbent substrate, the skin preferably having a height, measured along the main direction of extension of the absorbent substrate, that is substantially equal to the height of the absorbent substrate compressed in the main direction of extension;

the absorbent substrate further comprises a channel on the side surface, shaped so that the side skin is at least partially received in the channel when the absorbent substrate is compressed in the main direction of extension, the channel being integral with the rest of the absorbent substrate or being attached to the rest of the absorbent substrate;

the absorbent substrate has interlinked cells, with or without contact between the interlinked cells;

the cells have a shape selected from:
  a regular polyhedron, in particular a regular octahedron; and
  a regular truncated polyhedron, in particular a regular truncated octahedron;

the ridges of the cells have a length between 0.05 mm and 5 mm;

the ridges of the cells have a diameter between 0.02 mm and 3 mm;

the absorbent substrate comprises at least one among:
  open cells;
  semi-open cells; and the absorbent substrate further comprises cells that are closed.

According to another aspect, a packaging assembly for a cosmetic product is described comprising at least one receptacle intended to receive the cosmetic product, an absorbent substrate as described above in all its combinations, received in the receptacle, and a cover for closing the receptacle.

The packaging assembly may further comprise a housing, receiving the receptacle, a cosmetic product applicator member, and a cap for closing the housing.

A cosmetic product refill is also described for a packaging assembly for a cosmetic product, in particular as described above in all its combinations, comprising an absorbent substrate as described above in all its combinations, impregnated with cosmetic product in a sealed pouch.

The absorbent substrate may be received in a receptacle, preferably closed by a cover, inside the pouch.

According to yet another aspect, there is described a method for manufacturing an absorbent substrate as described above, in all its combinations, comprising at least a step a) of creating the ridges of the cells of the absorbent substrate by additive manufacturing.

The ridges of the cells may be created in step a) by 3D printing, in particular by SLS, FSL, stereolithography, or fused filament fabrication.

The method for manufacturing a packaging assembly for a cosmetic product may further comprise the steps consisting of:

producing an absorbent substrate by implementing a method as described above in all its combinations,
   providing at least one receptacle intended to receive the cosmetic product, and a cover suitable for closing the receptacle,
   placing the absorbent substrate in the receptacle,
   impregnating the absorbent substrate with cosmetic product, and
   closing the receptacle with the cover.

The manufacturing method may further comprise the steps consisting of:

providing a housing and a cap suitable for closing the housing,
   providing a cosmetic product applicator member,
   placing the receptacle and the cosmetic product applicator member in the housing, and
   closing the housing using the cap.

DESCRIPTION OF THE FIGURES DRAWINGS

The invention will be better understood from the following description, given with reference to the accompanying drawings, where:

FIG. 1 schematically represents a section view of a packaging assembly for a cosmetic product, with an absorbent substrate;

Figure 1:
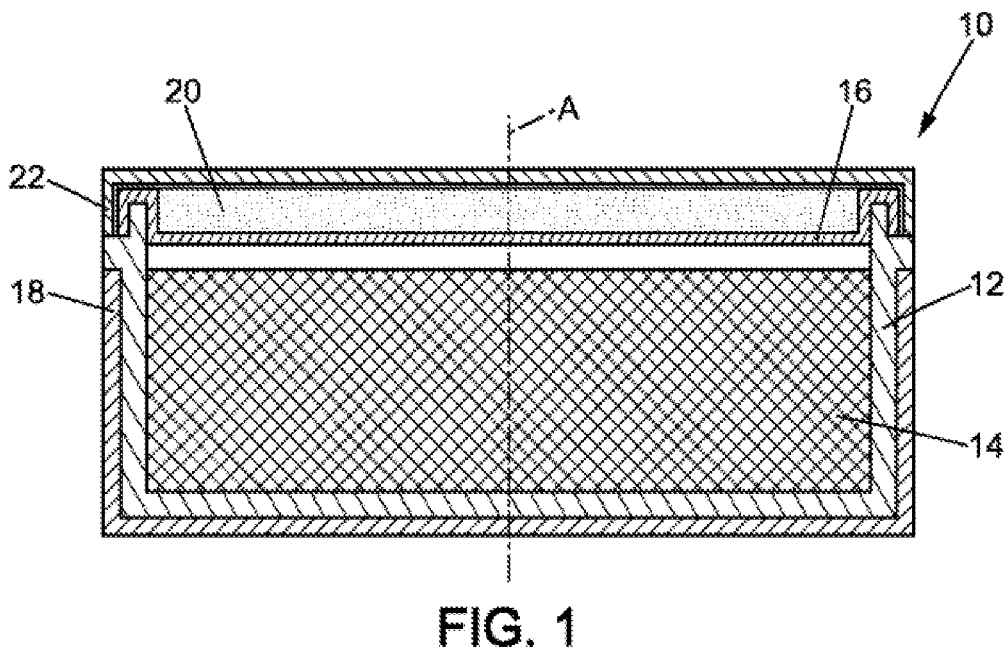
Figure 7:
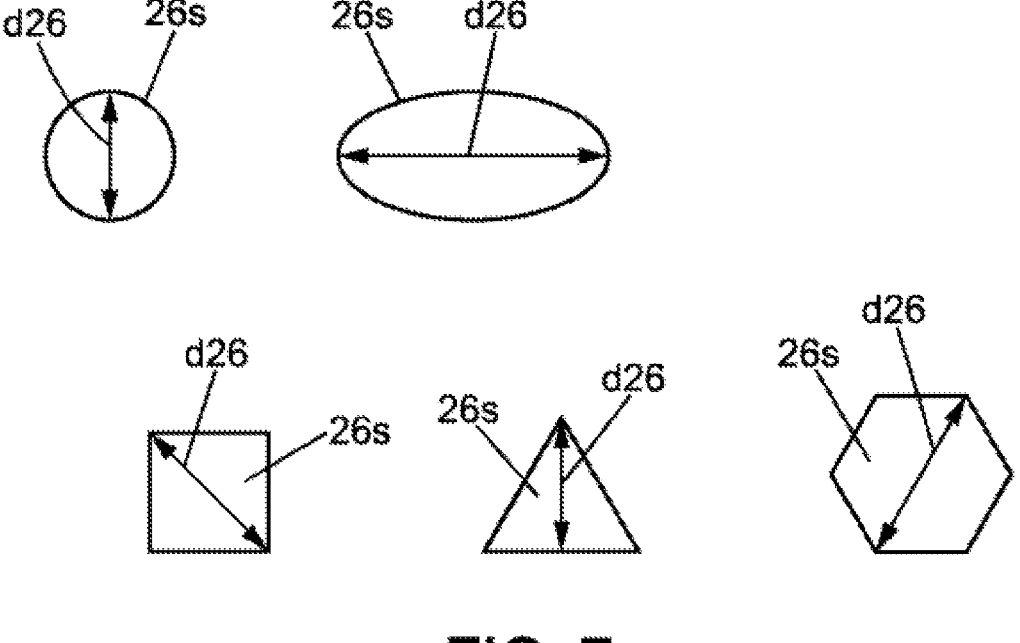
Figure 8:
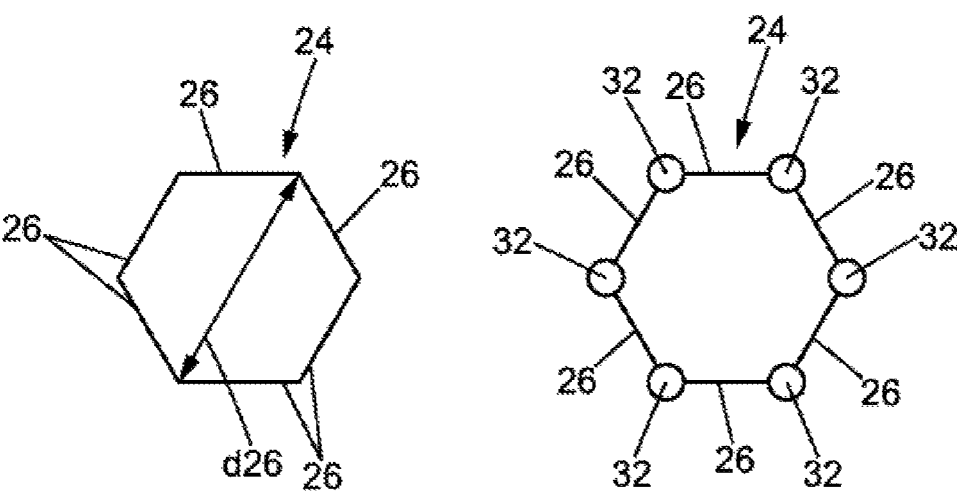
Figure 9:
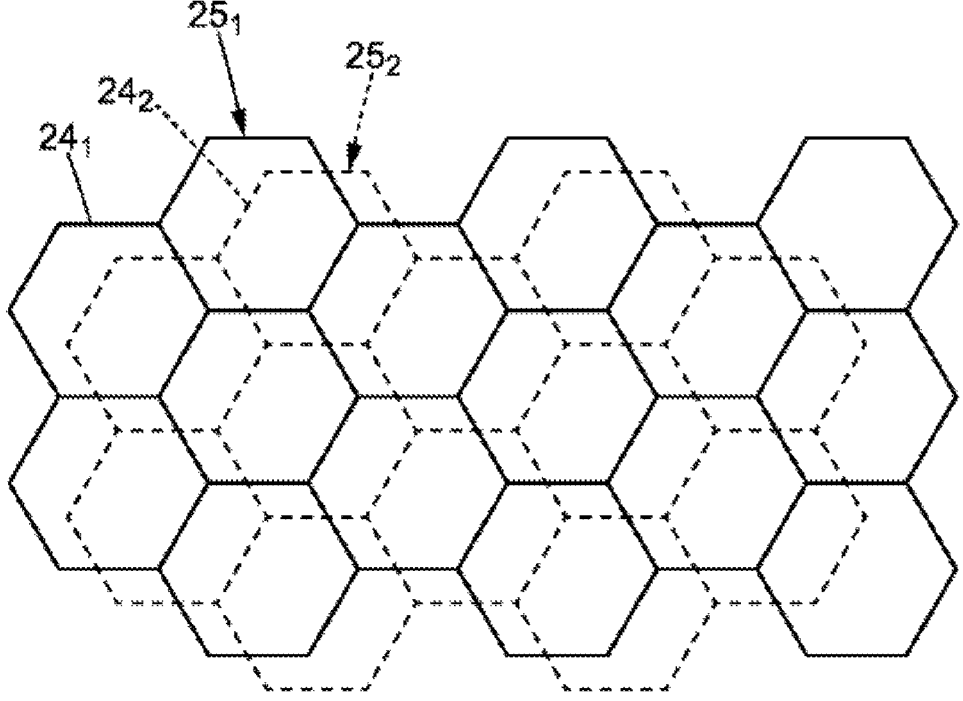
Figure 15:
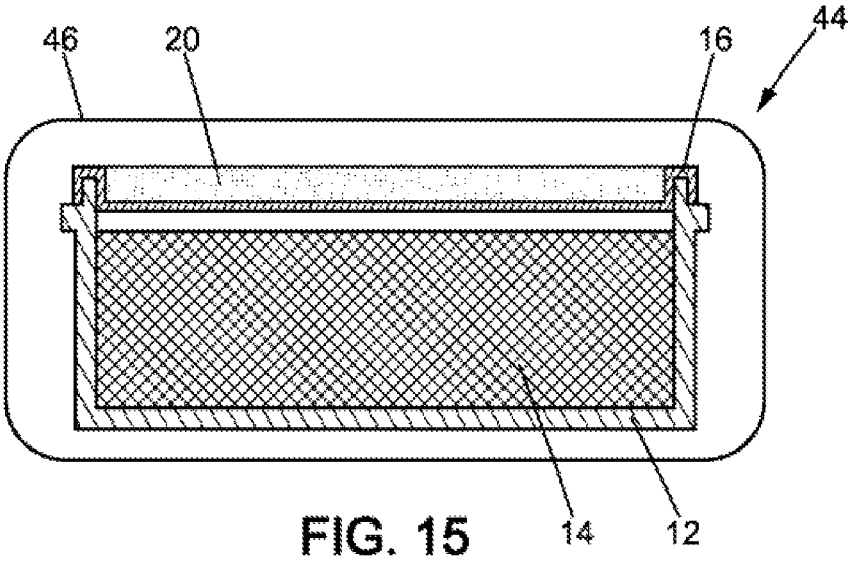
Figure 16:
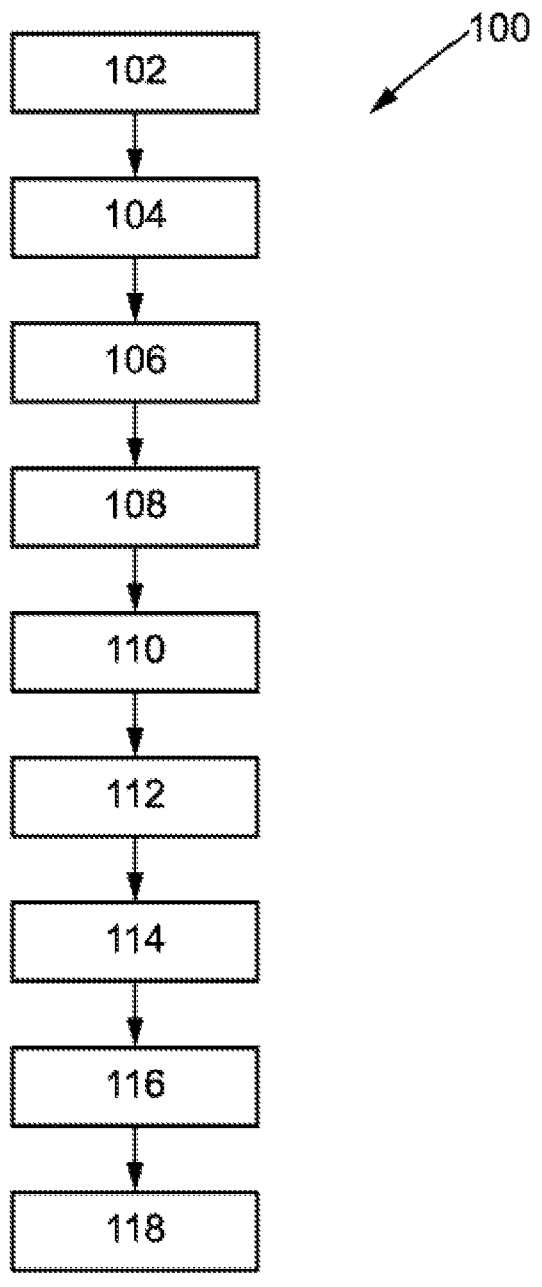

FIG. 7 schematically illustrates possible cross-sections of the ridges of the cells of the absorbent substrate of FIG. 1;

FIG. 8 schematically represents two possible cells of the absorbent substrate of FIG. 1;

FIG. 9 schematically illustrates a second example of a cell network which the absorbent substrate of FIG. 1 may have;

FIGS. 10 to 14 illustrate variations of the absorbent substrate of FIG. 1;

FIG. 15 schematically illustrates a section view of an exemplary cosmetic product refill for the packaging assembly for a cosmetic product of FIG. 1; and FIG. 16 is a flowchart of a manufacturing method for the packaging assembly of FIG. 1.

DETAILED DESCRIPTION OF THE DISCLOSURE

In the remainder of the description, elements that are identical or have an identical function bear the same reference notation. For the sake of brevity in the present description, these elements are not described within the context of each embodiment. On the contrary, only the differences between the embodiments are described.

FIG. 1 illustrates an example 10 of a packaging assembly for a cosmetic product. As illustrated, the packaging assembly 10 comprises a receptacle 12, an absorbent substrate 14 received in the receptacle 12, and a cover 16 for closing the receptacle 12.

"Absorbent substrate" is understood here to mean a substrate suitable for retaining the cosmetic product, for example by capillary action. The cosmetic product may be fluid, in particular liquid, more particularly viscous, or in powder form.

The absorbent substrate 14 is suitable for being impregnated with cosmetic product. Preferably, the absorbent substrate 14 is impregnated with cosmetic product—in other words it is retaining cosmetic product.

The absorbent substrate 14 is deformable (or flexible). In particular, the absorbent substrate is advantageously compressible by means of manual pressure by a user, for example using a thumb, advantageously in order to recover at least a portion of the cosmetic product with which it is impregnated. Compressible is understood here to mean that it is possible to minimize the volume of the absorbent substrate, in particular by manual pressure by a user, in particular by applying pressure with the thumb, where appropriate via an applicator member to be loaded with cosmetic product from the cosmetic product retained in the absorbent substrate 14.

The compression of the absorbent substrate makes it possible to recover at least a portion of the cosmetic product with which it is impregnated. In particular, from an absorbent substrate initially impregnated to saturation with cosmetic product, it is preferably possible to recover more than 80%, more preferably more than 90% of the cosmetic product with which the absorbent substrate is initially impregnated, by minimizing the volume of the absorbent substrate by compression.

In addition, here the packaging assembly 10 also comprises a housing 18 receiving the receptacle 12, a cosmetic product applicator member 20, and a cap 22 for closing the housing 18. Here, the applicator member 20 is housed in the cover 16 closing the receptacle 12. The receptacle 12 is for example removably received in the housing 18. It is then possible to replace the receptacle 12 in the housing 18 and thus refill the packaging assembly 10 with cosmetic product. According to one example, in this case the applicator member 20 can also be replaced, preferably concurrently with the receptacle 12.

The applicator member 20 is for example a sponge.

The receptacle 12 is arranged along a main axis A, vertical during use, which is coincident with the main axis of extension of the absorbent substrate 14.

In the example illustrated, the absorbent substrate 14 has a substantially cylindrical shape, having an axis of extension A. Here, the shape of the absorbent substrate is a cylinder of revolution. The cross-section of the absorbent substrate 14 may have a shape other than that of a disc. In general, the absorbent substrate 14 may have any shape.

The cover 20 may be fixed on the receptacle 12 by any suitable means accessible to those skilled in the art. In particular, the cover 20 may be screwed or clipped on the receptacle 12. Also, the cover 20 may be hinged on the receptacle 12 by means of a hinge (not illustrated) and/or provided with means (not illustrated) for locking the cover 20 in its position which closes the receptacle 12.

Similarly, the cap 22 may be fixed to the housing 18, directly or indirectly by any means accessible to those skilled in the art. The cap 22 may thus, in particular, be clipped or screwed either directly on the housing 18 or on the cover 16 of the receptacle 12. It is also possible for the cap 22 to be mounted on the housing 18 or on the cover 16 of the receptacle 12 by means of a hinge and/or be provided with means (not shown) for locking the cap 22 in its position which closes the housing 18.

Of course, other configurations of the packaging assembly 10 are also possible.

Figure 2:
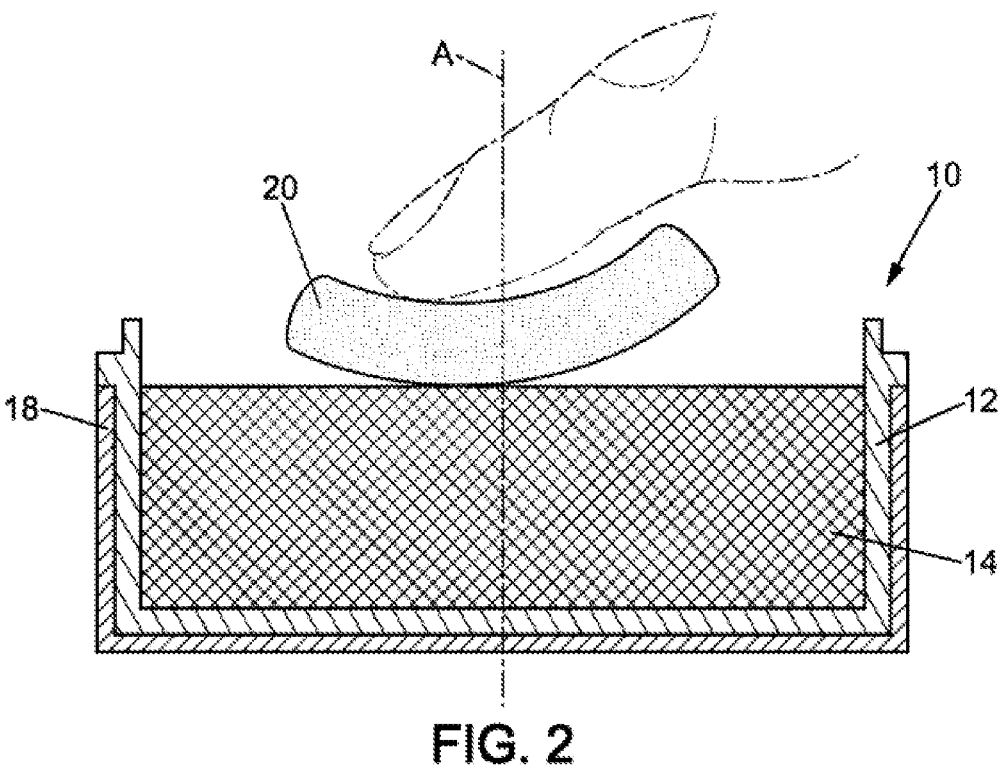
FIG. 2 illustrates the use of the packaging assembly for a cosmetic product of FIG. 1.

As can be seen in FIG. 2, such a packaging assembly 10 is used by applying the applicator member 20 against the absorbent substrate 14, such that the cosmetic product with which the absorbent substrate 14 is impregnated is released and impregnates the applicator member 20. The user can then apply the cosmetic product with which the applicator member 20 is impregnated, for example on his or her skin.

The cosmetic product may in particular be a liquid foundation, a semi-liquid foundation, a foundation in powder form, or any other cosmetic or self-care substance, such as perfume or makeup. The cosmetic product may in particular be selected from those requiring distribution through a sieve, a mesh, or a skin. The cosmetic product may also be selected from those which need to be reblended, such as a gloss, a self-tanner, a perfume incorporating a powder, mother-of-pearl, or particles. The cosmetic product may also be selected from self-care formulas, for example:

so-called "scrub" formulas, which comprise abrasive elements giving them an exfoliating effect, or multiphase self-care formulas, particularly of the "water in oil", "oil in water", or "water in silicone" type, for example, or multiphase makeup removal formulas.

The cosmetic product may also be selected from formulas incorporating surfactants, which can also be used for the generation of foam by means of the absorbent substrate.

The examples indicated above are not exhaustive and do not constitute a limiting list of products and uses.

The advantage of the absorbent substrate 14 is thus, firstly, to retain the more or less viscous or even powdery cosmetic product in the receptacle 12, and so prevent leaks or more generally the loss of cosmetic product.

However, another advantage of the absorbent substrate 14 can be in mixing the cosmetic product, immediately prior to the release and application of the cosmetic product. For example, the cosmetic product may be composed of insoluble elements and, at rest, have the form of an emulsion with different phases. The cosmetic product may in particular comprise solid particles in a fluid, and/or several fluids of different densities. In this case, pressing one or more times on the absorbent substrate 14, in the direction of the main axis of extension A of the absorbent substrate 14, makes it possible to mix the different phases and/or to distribute the particles in the cosmetic product. The applied cosmetic product thus has a more uniform texture.

Here, it is noteworthy that the absorbent substrate 14 has cells 24, defined by ridges 26 created by additive manufacturing. Preferably, a cell 24 is defined by a plurality of ridges 26. Cell is understood here to mean a geometric pattern formed by ridges and which is repeated to form a network. The network may be regular, if all the cells are identical, or irregular if the cells vary.

In a manner that is known per se, the term "additive manufacturing" is understood to mean methods for manufacturing by the addition of material. Additive manufacturing is advantageously computer-assisted. Additive manufacturing may in particular be carried out by shaping a part by the addition of material, for example by stacking successive layers. Additive manufacturing is thus in opposition to the removal of material or to molding processes which impose geometric constraints on their implementation, or to processes resulting from chemical reactions, such as those generally implemented to produce a sponge material, and for which the result is a random and/or irregular structure.

Additive manufacturing is sometimes called "three-dimensional printing" or "3D printing", especially by the general public.

Such an additive manufacturing process makes it possible to produce numerous variants of the absorbent substrate 14, exhibiting a large number of advantageous characteristics compared to a substrate made of sponge material or of woven or non-woven fabric.

Many processes can be implemented to create the ridges 26 of the cells 24 of the absorbent substrate 14, in particular:

selective laser sintering (or SLS): in this process, a three-dimensional model is created by successive two-dimensional layers of chosen thickness, a laser successively sweeping each layer in a tank of fine powder and sintering it;

selective laser melting (or SLM): in this process, a three-dimensional model is created by successive two-dimensional layers of chosen thickness, a laser successively sweeping each layer in a tank of fine powder and melting it.

Solidification of the model occurs directly after stopping the laser;

stereolithography (or SLA for "Stereolithography Apparatus"): in this process, a three-dimensional model is created by successive two-dimensional layers of chosen thickness, a pair of lasers successively sweeping each layer in a liquid bath and polymerizing it only at the intersection of the two laser beams;

fused filament fabrication (or FFF): in this process, a three-dimensional model is created by depositing a molten filament.

These manufacturing processes are selected in particular according to the material(s) used and/or the dimensions desired for the ridges 26 and/or cells 24.

In the case of the absorbent substrate 14, it may in particular be made of one among:

a polyamide, for example PA11, a polyethylene, a thermoplastic polyurethane or TPU, a polyaryletherketone or PAEK, and a metal or a metal alloy which may in particular be selected from:

aluminum or an aluminum alloy, cobalt or a cobalt alloy, chromium or a chromium alloy, in particular an alloy of cobalt and chromium, nickel or a nickel alloy, a stainless steel, and titanium or a titanium alloy.

With an additive manufacturing process, it is thus possible to create cells 24 which can retain the cosmetic product. To do this, the volume of each cell 24 is reduced. The volume of each cell is adapted to the formula to be contained. Additive manufacturing makes it possible in particular to adapt the size of the cell.

The volume of the cells 24 is thus adapted to the formula that they contain, in particular in order to enable them to store the cosmetic product, for example by capillary action.

The ridges 26 of the cells 24 have for example a length l26 of between 0.5 mm to 5 mm. The length of the ridges 26 of the cells 24 is chosen, within this interval, as a function of the formula contained.

Also, the ridges of the cells have, for example, a diameter d26 of between 0.02 mm and 3 mm. "Diameter of a ridge" is understood here to mean the largest dimension of the cross-section of a ridge.

The shape of the cells 24 can vary greatly. In practice, these cells 24 may take any shape that can be created by an additive manufacturing process and enabling the absorbent substrate 14 to store the cosmetic product, then release it by pressure on the absorbent substrate 14.

Figure 3:
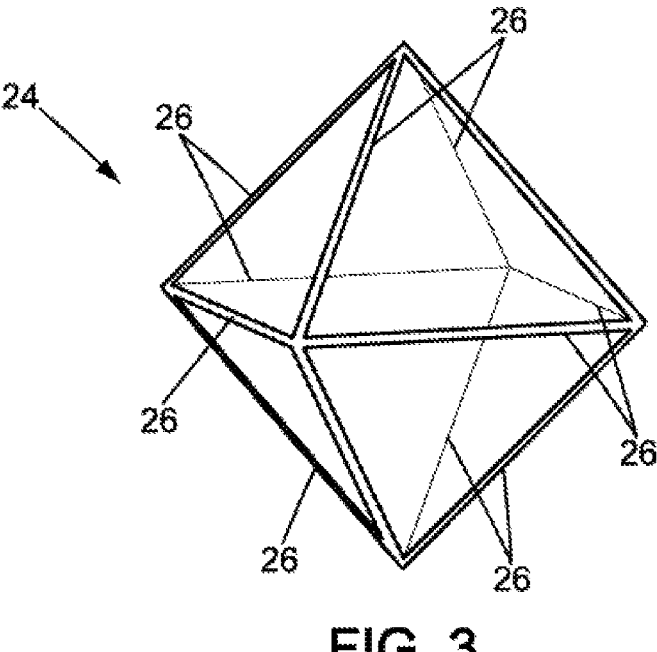
FIGS. 3 to 5 illustrate examples of cells which the absorbent substrate of FIG. 1 may have.
Figure 4:
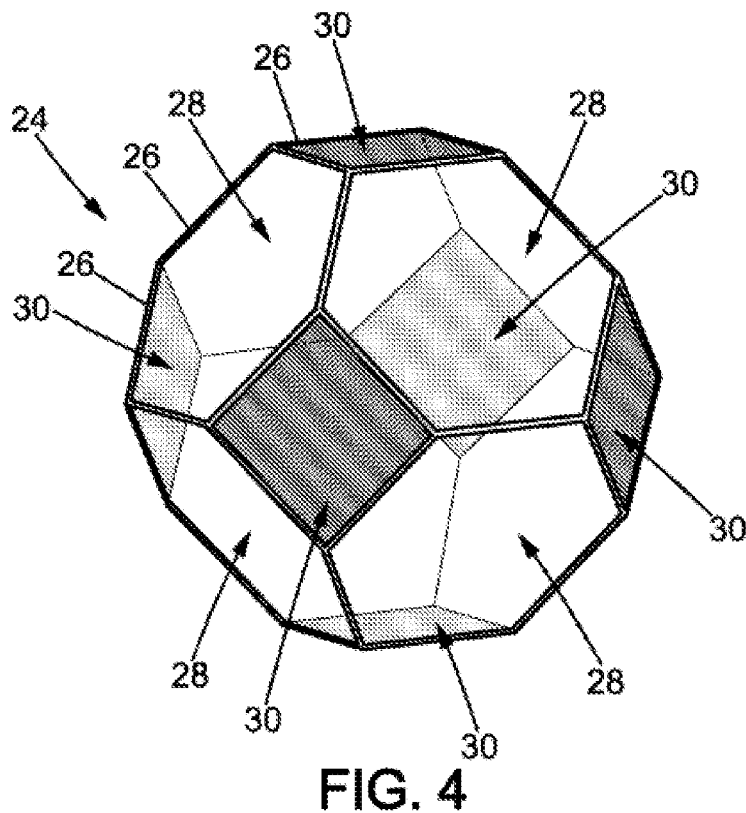

In particular, the cells 24 may be polyhedral. FIGS. 3 and 4 illustrate examples of such cells.

In FIG. 3, cell 24 has the shape of an octahedron. Here, for example, the cell is open, i.e. the space between the ridges 26 is empty.

In FIG. 3, cell 24 has the shape of a truncated octahedron. Here, the cell 24 shown is semi-open, i.e. certain surfaces 28 of the truncated octahedron formed by the ridges 26 are empty while other surfaces 30 of the truncated octahedron formed by the ridges 26 are filled.

In general and independently of the shape of the cells 24, they may be either open, or closed, or partially open (or semi-open). Also, in a same absorbent substrate 14, it is possible to create open cells and/or closed cells and/or semi-open cells. It should be noted here that with an additive manufacturing process, it is possible to very precisely define the open, closed, or semi-open cells. The creation of closed and/or semi-closed cells can make it possible to guide the flow of cosmetic product. For example, the closed and/or semi-closed cells are shaped to direct the flow of cosmetic product, in the event of pressure on the absorbent substrate along axis A, in the direction of axis A, towards the longitudinal ends. Additionally or alternatively, the closed and/or semi-closed cells are shaped to direct the flow of cosmetic product, in the event of pressure on the absorbent substrate along axis A, in a direction leading towards the side surface of the absorbent substrate 14.

According to a particularly advantageous embodiment, the cells 24 have a shape such that the ridges which define it can be substantially in the same plane when the absorbent substrate 14 is compressed in the direction of extension A. This has the advantage of reducing the "dead volume" of the cells 24 where cosmetic product can remain trapped when the absorbent substrate 14 is compressed.

Figure 5:
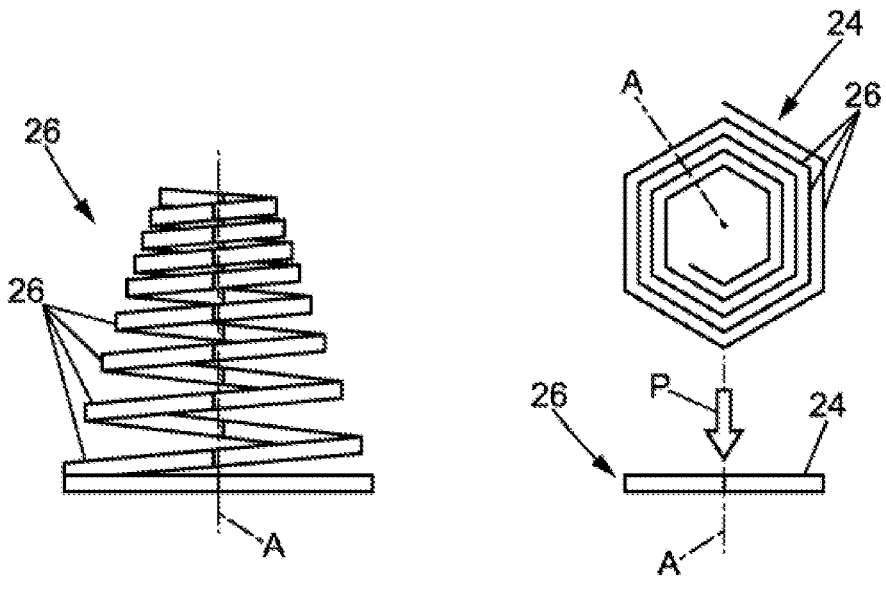

An example of such a cell 24 is illustrated in FIG. 5. In this figure, a cell 24 is defined by ridges 26 extending in the form of a frustoconical helix of axis A. Thus, in the event of compression of the cell 24, by pressure P along the direction of the axis of extension A of the cell 24, the cell is reduced to a spiral shape within a plane.

Figure 6:
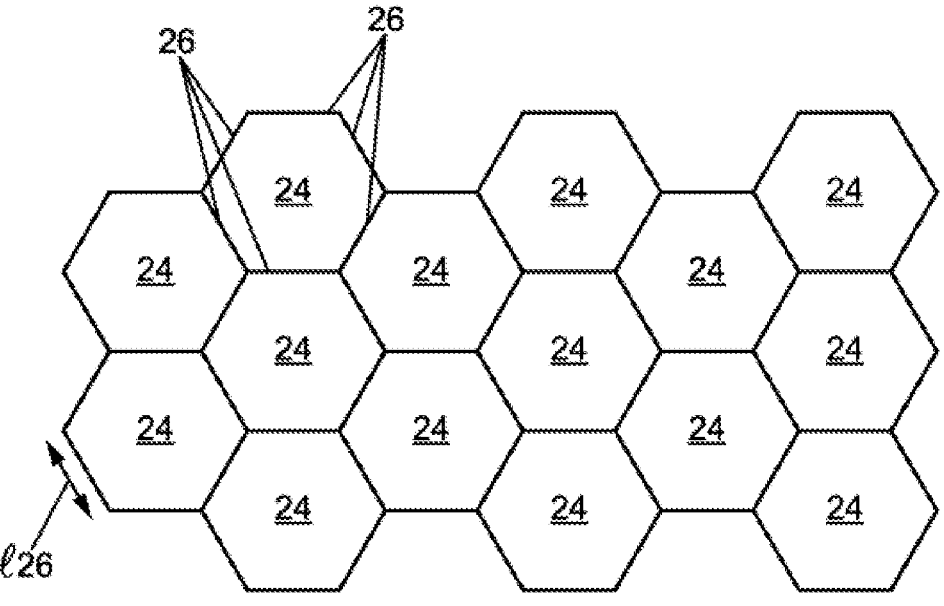
FIG. 6 schematically illustrates a network of cells which the absorbent substrate of FIG. 1 may have.

As illustrated in FIG. 6, the cells 24 may all be identical. The cells 24 may also be joined to each other, for example by sharing ridges 26 with neighboring cells 24. Alternatively, however, the cells 24 may be spaced apart from one another.

As can be seen in FIG. 7, the ridges 26 may in particular be cylindrical, having a polygonal cross-section 26s, in particular triangular, square, or hexagonal, or round or oblong. The cross-section of the ridges 26 may in particular be chosen to improve the mixing produced by means of the absorbent substrate 14 when the substrate is compressed. For this purpose, a polygonal cross-section appears preferred. Conversely, a cross-section not having angles appears preferable for increasing the volume of cosmetic product that the absorbent substrate can release when it is compressed.

Also, the ridges 26 may be of substantially constant cross-section along their entire length and be connected to each other directly, as illustrated on the left in FIG. 8. Directly is understood here to mean without any interposed structural element. In this case, the flexibility of the absorbent substrate 14 is provided by the flexibility of the ridges 26 themselves. In other words, to ensure that the absorbent substrate 14 can release cosmetic product, the ridges 26 should be dimensioned so that they can deform when a user applies pressure P on the absorbent substrate 14, for example with the thumb, directly or via the applicator member 20.

On the contrary, as illustrated on the right in FIG. 8, the ridges 26 may be interconnected by hinges 32. The hinges 32 may in particular be created by portions of reduced cross-section, in particular of smaller cross-section than the cross-section of the ridges 26. The hinges are also created by an additive manufacturing method, for example concurrently with the ridges 26 of the cells 24 of the absorbent substrate 14. In this case, it is possible to obtain the flexibility of the absorbent substrate simply by virtue of the hinges 32, the ridges 26 being sufficiently rigid so as not to be deformed in the event of pressure P from a user.

Alternatively, the flexibility of the absorbent substrate 14 is obtained by a combination of a flexibility of the ridges 26 and the presence of hinges 32 between these ridges 26.

Furthermore, as is schematically visible in FIG. 9, the cells 24 may form two networks $25_1$, $25_2$ of interlinked cells $24_1$, $24_2$. The cells $24_1$, $24_2$ of the two networks $25_1$, $25_2$ may be independent of one another, or conversely be connected to one another. Interlinked cells can make it possible to optimize the capabilities for mixing the formula, such mixing not being possible with other technologies. Also, interlinked cells can be used to optimize the flexibility of the absorbent substrate 14 by minimizing the compressive strength.

Here, the two networks $25_1$, $25_2$ are substantially identical, comprising identical cells $24_1$, $24_2$. Alternatively, however, the two networks $25_1$, $25_2$ may have different shapes. In particular, the cells $24_1$ of the first network $25_1$ may be different from the cells $24_2$ of the second network $25_2$.

Figure 10:
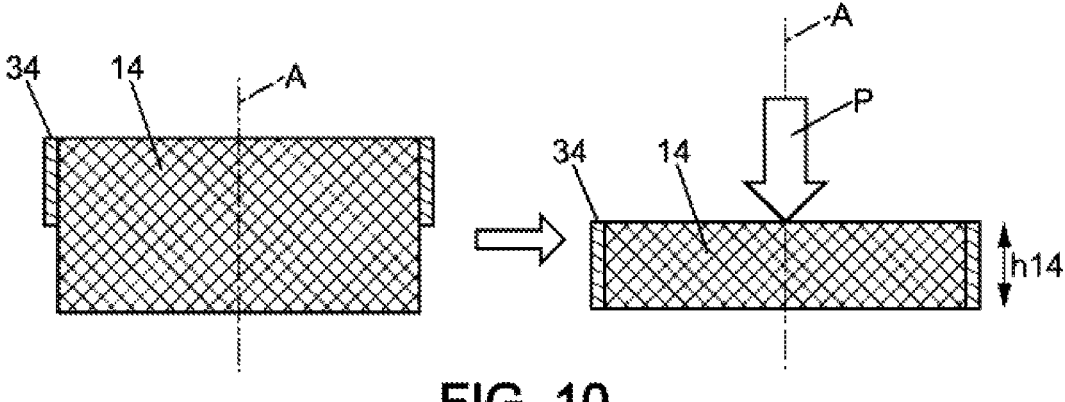

FIG. 10 represents a section view of another example of an absorbent substrate 14. This substrate differs from the one just described essentially in that it comprises a skin 34. Here this skin 34 extends over the side surface of the absorbent substrate 14. This skin may be produced separately and then attached to the absorbent substrate 14. Alternatively, however, this skin 34 is produced concurrently with the rest of the absorbent substrate 14, in particular with the ridges 26 of the cells 24.

Alternatively, the skin may be made of a textile, natural or synthetic, of fabric, natural or synthetic, of felt, or may be of synthetic skin.

The skin 34 may form an element for filtering or regulating the distribution of cosmetic product, for example by preventing, or conversely by allowing, the distribution of cosmetic product locally only.

Here the skin 34 is fluidtight (or impermeable). The skin 34 extends, as illustrated in FIG. 10, for a height h14 corresponding to the minimum height of the absorbent substrate 14 when it is compressed under the effect of a pressure P directed along axis A. This skin thus makes it possible to reduce the amount of cosmetic product which escapes by the side face of the absorbent substrate 14 when a user compresses it in direction A. Advantageously, this skin 34 is fixed on the absorbent substrate 14 in the vicinity of its upper end during use.

The skin 34 may be connected to the absorbent substrate 14, at one or more points or along the entire height of the skin 34. In order to improve tidiness during use of the cosmetic product, the absorbent substrate 14 may also be provided with a ring having a closed or partially closed structure, on the first few millimeters of the skin, thus forming a ring around the absorbent substrate 14. This can make it possible to form an anti-fouling protection ring on the side surface of the absorbent substrate, around the formula distribution surface.

Figure 11:
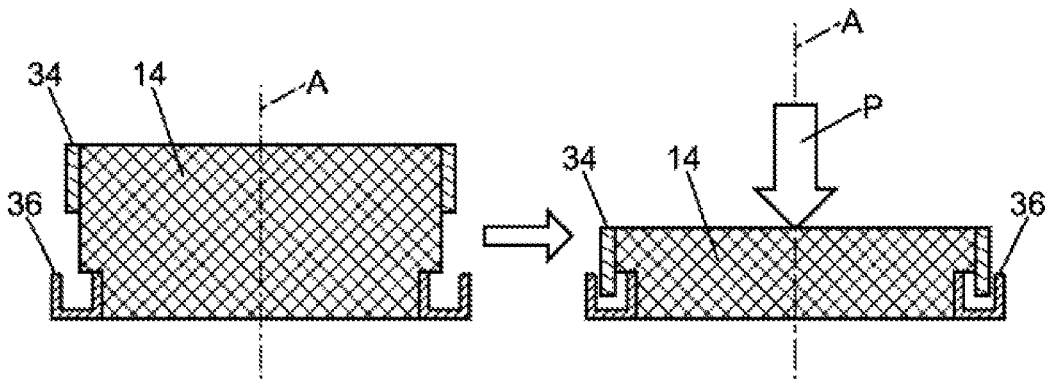

In FIG. 11, the absorbent substrate has, in addition to a skin 34, a channel 36 identical to the one presented above. The channel 36 essentially has an annular shape with a U cross-section. The channel 36 here is fixed to the lower end of the absorbent substrate 14 during use. Here again, the channel 36 may be created separately from the rest of the absorbent substrate 14 and then attached thereto, or concurrently with the rest of the absorbent substrate, in other words with the ridges 26 of the cells 24, and preferably the skin 34 where appropriate. As can be seen in FIG. 11, the channel 36 is shaped to at least partially receive the skin 34 in the event of pressure P on the absorbent substrate 14 in direction A. Here again, the cooperation of the skin 34 received in the channel 36 aims to reduce or even prevent the flow of cosmetic product through the side face of the absorbent substrate, in the event of pressure P by a user on the absorbent support 14 in direction A. The cooperation of the skin 34 and the channel 36 in fact increases the head loss to be overcome by the cosmetic product in order to be able to flow through the side face of the absorbent substrate 14.

Figure 12:
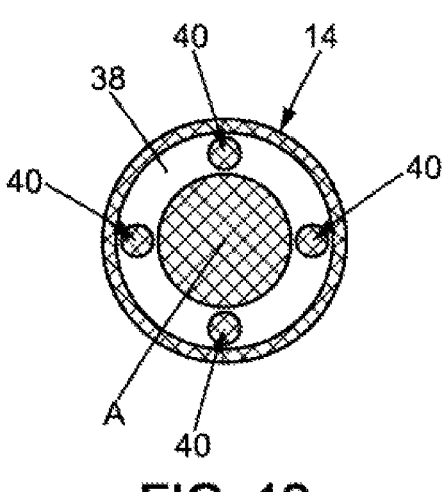
Figure 13:
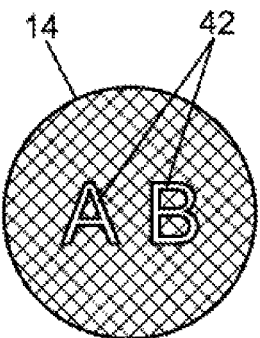

In FIG. 12, a skin 38 is placed on an end surface—in this case the upper surface—of the absorbent substrate 14. This skin 38 is also fluidtight to the cosmetic product. This skin 38 may also be created separately and attached to the absorbent substrate 14 or created concurrently with the rest of the absorbent substrate, in particular with the ridges 26 of the cells 24, and preferably the skin 34 on the side surface of the absorbent substrate 14 and/or the channel 36, where appropriate. As an example, the skin 38 illustrated in FIG. 12 has an annular shape and has through-holes 40. Thus, the skin 38 reduces the passage of cosmetic product from the cells 24 to the upper surface of the absorbent substrate 14. Such a skin 38 thus makes it possible to control the quantity of cosmetic product distributed by the absorbent substrate 14 when it is compressed in its main direction A of extension.

Additionally or alternatively, a skin 42 may be created, as described above, in particular on the upper surface of the absorbent substrate 14. This skin 42 makes it possible in particular to obtain an aesthetic effect and/or to indicate a brand, text, logo, design, or any other communicating sign. As previously indicated, this skin may also act as a "flow reducer" in the distribution of the contained formula, with the aim to optimize recovery of the formula on the applicator member.

Figure 14:
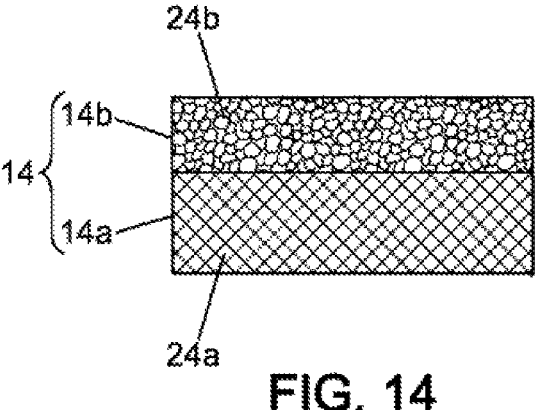

As illustrated in FIG. 14, the absorbent substrate 14 may have a first layer 14*a* in which the absorbent substrate 14 has first cells 24*a*, and a second layer 14*b* in which the absorbent substrate 14 has second cells 24*b* different from the first cells 24*a*. In particular, the first and second cells 24*a*, 24*b* are of different shapes and/or of different volumes. In particular, the second cells 24*b* located towards the top of the absorbent substrate 14 from where the cosmetic product is collected, have a smaller volume than the first cells 24*a*.

More generally, the cells 24 of the absorbent substrate 14 may not all be identical. The cells 24 of the absorbent substrate 14 may in particular have a volume which decreases the closer they are to the surface of the absorbent substrate 14 from where the cosmetic product is collected.

As illustrated in FIG. 15, the packaging assembly 10 for a cosmetic product can be refilled by means of a refill 44. This cosmetic product refill 44 comprises, as illustrated in FIG. 15, an absorbent substrate 14, as described above, in all its variants, impregnated with cosmetic product in a sealed pouch 46. Here, the refill 44 further comprises a receptacle 12, receiving the absorbent substrate 14, inside the pouch 46, closed by a cover 16 and receiving an applicator member 20.

Furthermore, FIG. 16 schematically represents a flow-chart of a method 100 for manufacturing a packaging assembly for a cosmetic product 10.

This manufacturing method comprises a step 102 of creating the ridges 26 of the cells 24 of the absorbent substrate 14 by additive manufacturing.

As indicated above, the additive manufacturing process implemented may in particular be a selective laser sintering process, a selective laser melting process, a stereolithography process, or a fused filament fabrication process.

Furthermore, the absorbent substrate 14 may also be partially or completely covered by an element for filtering or regulating the distribution of cosmetic product, the regulating element allowing, or on the contrary locally preventing, the distribution of cosmetic product. This element for filtering or regulating the distribution of cosmetic product, like the skin 34 described above, may in particular be made of a textile, natural or synthetic, of fabric, natural or synthetic, of felt, or of synthetic skin. The filtering element may or may not be attached to the absorbent substrate 14.

The absorbent substrate 14 may also be covered to improve the feel for a user.

The method 100 continues with a step 104 of providing at least one receptacle 12 intended to receive the cosmetic product, and a cover 16 suitable for closing the receptacle 12.

It should be noted here that the absorbent substrate 14 may be covered before, during, or after its integration into the receptacle 12.

In step 106, the absorbent substrate 14 is placed in the receptacle 12, and in step 108, the absorbent substrate 14 is impregnated with cosmetic product. In step 110, the receptacle 12 is closed with the cover 16.

In step 112, a housing 18 and a cap 22 capable of closing the housing 18 are then provided. In step 114, a cosmetic product applicator member 20 is provided. In a step 116, the receptacle 12 and the cosmetic product applicator member 20 are placed in the housing 18. Finally, in step 118, the housing 18 is closed using the cap 20.

The invention is not limited solely to the embodiments described above with reference to the figures, but on the contrary is capable of numerous variants accessible to those skilled in the art. In particular, unless otherwise stated, the various embodiments described can be combined.

The geometry of the cells is preferably chosen to minimize their volume in the event of compression of the absorbent substrate, thus reducing the dead volume of the absorbent substrate.

According to a variant not shown, the absorbent substrate has different cells in a same layer extending perpendicularly to axis A. The layer extending perpendicularly to axis A may in particular correspond to the entire volume of the absorption substrate. In this case, the cells depend only on their radial position with respect to axis A and are independent of their vertical position, measured along axis A. For example, the cells become increasingly smaller, or conversely increasingly larger, in the radial direction from axis A towards the side surface of the absorbent substrate 14. Increasingly smaller cells as they approach the side surface of the absorbent substrate 14 make it possible in particular to gradually increase the head loss in the flow of cosmetic product approaching the side surface of the absorbent substrate. It is thus possible to reduce the amount of cosmetic product escaping from the absorbent substrate 14 via the side surface.

In the example described, the absorbent substrate 14 is used as a cosmetic product reservoir/mixer. Alternatively, the absorbent substrate may be used as a cosmetic product applicator member. In this case, it may be integrated into a cosmetic product application assembly comprising a reservoir and an absorbent substrate as applicator member, the applicator member advantageously being separated from the contents of the cosmetic product reservoir.

The invention claimed is:

1. A packaging assembly for a cosmetic product, comprising at least one receptacle intended to receive the cosmetic product, an absorbent substrate, received in the receptacle, and a cover for closing the receptacle, the packaging assembly further comprising a housing, receiving the receptacle, a cosmetic product applicator member, and a cap for closing the housing, wherein the absorbent substrate has cells defined by ridges, the ridges being raised or protruding structures each cell being a geometric shape formed by the ridges which is repeated to form a network, the ridges being created by additive manufacturing, the ridges being cylindrical with a cross-section chosen from a group consisting of a polygonal cross section, a round cross section and an oblong cross-section.

2. The packaging assembly according to claim 1, wherein the ridges are created by selective laser sintering, selective laser melting, stereolithography, or fused filament fabrication.

3. The packaging assembly according to claim 1, wherein the absorbent substrate extends in a main direction, the ridges being shaped to extend substantially in a same plane when the absorbent substrate is compressed by pressure in the main direction.

4. The packaging assembly according to claim 1, wherein the ridges are interconnected by hinges, also created by additive manufacturing.

5. The packaging assembly according to claim 1, the absorbent substrate extending in a main direction, wherein the absorbent substrate has a first layer in which the absorbent substrate has first cells and a second layer in which the absorbent substrate has second cells different from the first cells.

6. The packaging assembly according to claim 5, wherein the first and second cells are:

of different shapes; and/or of different volumes.

7. The packaging assembly according to claim 1, the absorbent substrate extending in a main direction, wherein the absorbent substrate has at least one layer, oriented perpendicularly to the main direction, said at least one layer having third cells and fourth cells, the fourth cells being different from the third cells.

8. The packaging assembly according to claim 7, wherein the third and fourth cells are:

of different shapes; and/or of different volumes.

9. The packaging assembly according to claim 1, wherein the absorbent substrate comprises a skin on at least one of its surfaces.

10. The packaging assembly according to claim 9, wherein the absorbent substrate is of substantially cylindrical shape, extending in a main direction of extension, wherein a side skin is provided on a side face of the absorbent substrate.

11. The packaging assembly according to claim 10, wherein the absorbent substrate further comprises a channel on the side face, shaped so that the side skin is at least partially received in the channel when the absorbent substrate is compressed in the main direction of extension.

12. The packaging assembly according to claim 1, wherein the absorbent substrate has interlinked cells.

13. The packaging assembly according to claim 1, wherein the cells have a shape selected from:

a regular polyhedron; and a regular truncated polyhedron.

14. The packaging assembly according to claim 1, wherein the ridges of the cells have a length between 0.05 mm and 5 mm.

15. The packaging assembly according to claim 1, wherein the ridges of the cells have a diameter between 0.02 mm and 3 mm.

16. The packaging assembly according to claim 1, wherein the absorbent substrate comprises at least one among:

open cells;

semi-open cells.

17. The packaging assembly according to claim 16, wherein the absorbent substrate further comprises cells that are closed.

18. A method for manufacturing a packaging assembly for a cosmetic product according to claim 1, comprising the steps consisting of:

producing an absorbent substrate by implementing a method comprising at least a step a) of creating the ridges of the cells of the absorbent substrate by additive manufacturing, wherein the ridges of the cells are created in step a) by 3D printing, providing at least one receptacle intended to receive the cosmetic product, and a cover suitable for closing the receptacle, placing the absorbent substrate in the receptacle, impregnating the absorbent substrate with cosmetic product, and closing the receptacle with the cover.

19. The manufacturing method according to claim 18, further comprising the steps consisting of:

providing a housing and a cap suitable for closing the housing, providing a cosmetic product applicator member, arranging the receptacle and the cosmetic product applicator member in the housing, and closing the housing using the cap.

*    *    *    *    *